(12) United States Patent
Dow (10) Patent No.: US 8,343,463 B2
(45) Date of Patent: Jan. 1, 2013

(54) OPTICAL IMAGING AGENT

(75) Inventor: William Dow, Irvine, CA (US); Karen B. Dow, legal representative, Irvine, CA (US)

(73) Assignee: Numira Biosciences Inc., Salt Lake City, UT (US)

( * ) Notice: Subject to any disclaimer, the term of this patent is extended or adjusted under 35 U.S.C. 154(b) by 334 days.

(21) Appl. No.: 12/848,911

(22) Filed: Aug. 2, 2010

(65) Prior Publication Data

US 2011/0027191 A1 Feb. 3, 2011

Related U.S. Application Data

(60) Provisional application No. 61/230,574, filed on Jul. 31, 2009.

(51) Int. Cl.
*A61B 5/00* (2006.01)
(52) U.S. Cl. .......................................... 424/9.6; 424/9.1
(58) Field of Classification Search .................. None
See application file for complete search history.

(56) References Cited

U.S. PATENT DOCUMENTS

| 6,423,547 B1 * | 7/2002 | Rajagopalan et al. ......... 424/9.6 |
| 2005/0170363 A1 | 8/2005 | Reddington ...................... 435/6 |
| 2005/0214833 A1 | 9/2005 | Carter .............................. 435/6 |

FOREIGN PATENT DOCUMENTS

EP 0591820 A1 4/1994

OTHER PUBLICATIONS

Berge et al., J. of Pharmaceutical Science, vol. 66, p. 1-19 (1977).
Bouizar et al., Eur. J. Biochem., vol. 155, p. 141-147, (1986.).
Browning, et al., J. Immunol., vol. 143, p. 1859-1867 (1989).
Cardullo, R.A. et al., "Detection of Nucleic Acid Hybridization by Nonradiative Fluorescence Resonance Energy Transfer," Proc. Natl. Acad. Sci. US, vol. 85, p. 8790-8794, (1988).
Dexter, D.L., "A Theory of Sensitized Luminescence in Solids," J. of Chemical Physics, vol. 21, p. 836-850 (1953).
Ernst, L.A., et al., "Cyanine Dye Labeling Reagents for Sulfhydryl Groups," Cytometry, vol. 10, p. 3-10 (1989).
Grimm, J., et al., "Use of Gene Expression Profiling to Direct in Vivo Molecular Imaging of Lung Cancer," Proc. Natl. Acad. Sci. USA, vol. 102, p. 14404-14409, (2005).
Harris, J.B., "Myotoxic Phospholipases A2 and the Regeneration of Skeletal Muscles," Toxicon vol. 42, p. 933-945 (2003).
Hochstrasser, R.A. et al., "Distance Distribution in a Dye-Linked Oligonucleotide Determined by Time-Resolved Fluorescence Energy Transfer," Biophysical Chemistry, vol. 45, issue 2, p. 133-141, (1992).

Jung et al., Biochem. Biophys. Acta, vol. 761, p. 152-162.
Joshi, et al., J. Biol. Chem., vol. 265, p. 14518-14525 (1990).
Luker, G.D., et al., "Optical Imaging: Current Applications and Future Directions," J. Nucl. Med., vol. 49, p. 1-4, (2008).
Mujumdar, R. B., "Cyanine Dye Labeling Reagents: Sulfoindocyanine Succinimidyl Esters" Bioconjugate Chem., vol. 4, p. 105-111 (1993).
Nishijo, K., et al., "Biomarker System for Studying Muscle, Stem Cells, and Cancer in Vivo," FASEB J., vol. 23, No. 8, p. 2681-2690 (2009).
Ochoa, o., et al., "Delayed Angiogenesis and VEGF Production in CCR2-/- Mice During Impaired Skeletal Muscle Regeneration," Am. J. Physiol. Regul. Integr. Comp. Physiol, vol. 293, No. 2, p. R651-R661 (2007).
Park, et al., J. Biol. Chem., vol. 261, p. 205-210 (1986).
Prajapati, S.I., et al., "Near-Infrared Imaging of Injured Tissue in Living Subjects Using IR-820," Mol. Imaging, vol. 8, p. 45-54 (2009).
Selvin, P.R., "Fluorescence Resonance Energy Transfer," Methods in Enzymology, vol. 246, p. 300-334 (1995).
Steinberg, I., "Long-Range Nonradiative Transfer of Electronic Excitation Energy in Proteins and Polypeptides," Annual Review of Biochemistry, vol. 40, p. 83-114 (1971).
Stryer, L., "Fluorescence Energy Transfer as a Spectroscopic Ruler" Annual Review of Biochemistry, vol. 47, p. 819-846 (1978).
Taniguchi, E., et al., "Bortezomib Reverses a Post-Translational Mechanism of Tumorigenesis for Patched1 Haploinsufficiency in Medulloblastoma," Pediatr. Bood & Cancer, vol. 53, issue 2, p. 136-144 (2009).
Terpetschnig, E., et al., "Synthesis of Squaraine-*N*-Hydroxysuccinimide Esters and their Biological Application as Long-Wavelength Fluorescent Labels," Analytical Biochemistry, vol. 217, issue 2, p. 197-204 (1994).
Wang, G.T., et al., "Design and Synthesis of New Fluorogenic HIV Protease Substrates Based on Resonance Energy Transfer," Tetrahedron Letters, vol. 31, issue 45, p. 6493-6496 (1990).
Wang, Y., et al., "Rapid Sizing of Short Tandem Repeat Alleles Using Capillary Array Electrophoresis and Energy-Transfer Fluorescent Primers," Analytical Chemistry, vol. 67, issue 7, p. 1197-1203 (1995).
Zarling et al., J. Immunol., vol. 913-920, (1980).

* cited by examiner

*Primary Examiner* — David J Blanchard
*Assistant Examiner* — Daniel F Coughlin
(74) *Attorney, Agent, or Firm* — Morgan, Lewis & Bockius LLP (57) ABSTRACT

The near-infrared wavelengths (700 nm-900 nm) are a suitable optical window for light penetration and deep tissue imaging. The present invention provides a near-infrared fluorescent blood pool contrast agent. The agent is of use to detect and quantify pathological capillary leak in live animals, e.g., serially imaging of traumatized tissue (muscle) as well as tumors.

2 Claims, 4 Drawing Sheets

Supplementary Figure-S1

A

B

OPTICAL IMAGING AGENT

CROSS-REFERENCE TO RELATED APPLICATIONS

This application claims benefit of priority to U.S. Provisional Patent Application Ser. No. 61/230,574, filed Jul. 31, 2009, which is hereby incorporated by reference in its entirety for all purposes.

BACKGROUND OF THE INVENTION

Preclinical and clinical fluorescence optical imaging instruments are increasingly utilized to obtain biological information on the path from gene to clinic (1). Skin and red blood cell autofluorescence occurs to some extent at all excitation wavelengths in visible wavelength range of light (400-700 nm). Due to this background signal, the quantification of fluorescence signals for in vivo imaging can be a difficult task when working in this range. To achieve better signal: background and increasingly accurate quantitative imaging in vivo, working within the near-infrared (NIR) wavelength range (700-900 nm) is desirable. In this spectral region, light absorption and scattering by physiologically abundant molecules such as hemoglobin, oxyhemoglobin, deoxyhemoglobin is minimized (2). NIR fluorescent contrast agents developed for in vivo optical imaging provide novel opportunities for pre-clinical diagnostic imaging in deep tissues (2). In this report we describe a novel, inexpensive near-infrared blood pool contrast agent and its utility in detecting capillary leak in animal models or muscle injury and cancer.

SUMMARY OF THE INVENTION

The present invention provides a new class of macromolecular optical contrast agents, compositions incorporating these agents and methods of using these agents in optical imaging modalities. Of interest in the present invention are contrast agents used for imaging the blood pool and monitoring its movement. Optical imaging assisted by such agents is useful for such procedures as assessments of relative tissue blood volume, estimation of tissue perfusion, and detection of abnormal capillary permeability. Clinical applications include assessments of myocardial and cerebral ischemia, pulmonary embolism, transplants, and neoplasia. To be useful as blood-pool markers, the contrast agents must remain in the pool rather than leaving it through such means as diffusion into extravascular compartments or glomerular filtration. A requisite property of contrast agents is therefore a relatively high molecular weight, which prevents the agents from diffusing through normal capillaries and glomerular endothelium. A further advantage of the agents of the invention is that the prolonged intravascular retention of these agents permits imaging of the blood pool in multiple body regions without repeated dosing, thereby eliminating the need for critical timing of the imaging.

In an exemplary embodiment, the macromolecular agent of the invention is of a size that allows its retention within healthy vasculature but allows it to penetrate damaged or poorly formed vasculature; penetrating the basement membrane and "leaking into the interstitium surrounding the vasculature. This "leak" gives rise to a detectable signal in the interstitium that would not be present, or would be present to a lesser degree, in a healthy tissue.

In an exemplary embodiment, the contrast agent of the invention comprises a fluorophore linked, through a linker, to a carrier molecule. The fluorophore can be selected based on the optimization of one or more of its characteristics, e.g., water-solubility, quantum yield, absorbance maximum, emission maximum, stability, and the like. Similarly, the linker is generally selected for a desired property, e.g., the ease of converting its precursor(s) into a linker joining the carrier molecule and the fluorophore, water-solubility, stability (or lack thereof under selected biological conditions), lack of quenching of the fluorophore, and the like. The carrier molecule can be a species that simply increases the molecular size or weight of the fluorophore or it can have properties that enhance the delivery of the contrast agent of the invention to a particular tissue (or prevent or retard its delivery to a particular tissue). Natural and synthetic polymers are exemplary choices for the carrier. In an exemplary embodiment, the carrier molecule is a polysaccharide.

In various embodiments, the present invention provides macromolecular optical imaging agents. In a representative embodiment, the invention provides a compound having a structure according to Formula I:

$$X-L^1-F \qquad (I)$$

wherein X is a carrier molecule. The symbol $L^1$ represents a linker selected from a bond ("zero-order"), substituted or unsubstituted alkyl, substituted or unsubstituted heteroalkyl, substituted or unsubstituted aryl and substituted or unsubstituted heteroaryl. F is a fluorophore.

In an exemplary embodiment, X is a polysaccharide, e.g., cyclodextrin, $L^1$ is a substituted or unsubstituted alkyl linker or substituted or unsubstituted heteroalkyl linker and F is a cyanine, e.g., indocyanine, e.g., indocyanine green. In an exemplary embodiment, the linkage fragment joining the cyclodextrin to the linker includes an amine moiety, e.g., the linker is an alkyl amine. In various embodiments, the linkage fragment joining the linker to the fluorophore is a sulfonamide. In various embodiments, the fluorophore has a maximum absorbance in the range of about 650 nm to about 1200 nm, for example, from about 700 nm to about 900 nm.

The invention also provides pharmaceutical formulations including the contrast medium of the invention. An exemplary formulation is a diagnostic formulation and the agent is present in an amount sufficient to produce a detectable signal in an optical imaging experiment when the formulation is administered to a subject. In various embodiments, the detectable signal is attributible the contrast agent of the invention concentrating into an intersititial space of a disease or injured tissue, and the agent is present in the formulation of the invention in sufficient amount to provide such detectable signal.

The contrast agents of the invention are of use in clinical and experimental optical imaging of regions of injury or disease. In exemplary embodiments, the contrast agents are of use to image regions of neoplastic growth (e.g., cancer), inflammation, degeneration (e.g., arthritis) and injury. The contrast agents are of use to assess the utility of therapeutic regimens (e.g., pharmaceutical, surgical) to treat injury and disease.

Other objects, advantages and aspects of the present invention will be apparent from the detailed description below.

BRIEF DESCRIPTION OF FIGURES

FIG. 2 Monitoring myoinjury using 1.
(A) Hairless$^{SKH1/SKH1}$ mouse serial images after injury of right (R) hind limb with intramuscular cardiotoxin injection; the left (L) hind limb was not injected. The images are displayed with a minimum-maximum scale of $5\times10^9$ to $2\times10^{10}$ photons/s/cm²/steradian. On the first image right and left regions of interest are shown as dotted lines. First image is prior to intraperitoneal injection of 1; times thereafter are labeled in reference to 1 injection and cardiotoxin was injected 1 hour after 1 injection. (B) Paired difference of injected hind limb and non-injected hind limb, time on x-axis measured after 1 injection (arrow); cardiotoxin injection into the right hind limb denoted by the arrowhead. Inset graph demonstrates an expanded view of the early time points immediately following 1 and cardiotoxin. All paired difference measurements from 2-168 hours were statistically significantly elevated compared to baseline. * indicates p<0.001, ns stands for not statistically significant. Error bars, s.d.; n=3 mice.

FIG. 3. In vivo imaging of tumor tissues using 1. Three transgenic mice were imaged 24 hours after injection of 100 μl of 1 intravenously through the tail vein. (A) Myf6$^{ICNm/WT}$ Pax3$^{P3Fm/P3Fm}$ Trp53$^{F2-10/F2-10}$ Rb1$^{Flox/Flox}$ mouse bearing an alvelolar rhabdomyosarcomas within the neck The image has been adjusted at a minimum-maximum scale of $5.5\times10^9$ to $9\times10^9$ photons/s/cm²/steradian. Desmin and Myogenin confirm diagnosis, whereas Trichrome demonstrates collagen rich stoma. Black arrowheads, capillaries. (B) Pax7$^{CreER/WT}$ Trp53$^{F2-10/F2-10}$ mouse with an embyonal rhabdomyosarcoma in the back. The diagnosis was confirmed by desmin and myogenin immunoreactivity. The image has been adjusted at a minimum-maximum scale of $6.42\times10^9$ to $1.3\times10^{10}$ photons/s/cm²/steradian. (C) Pax7$^{CreERp/WT}$ PTC1$^{F1-2m/WT}$ Trp53$^{F2-10/F2-10}$ mouse with a poorly differentiated spindle cell sarcoma involving the face. The image is thresholded between a minimum-maximum scale of $3\times10^9$ to $6\times10^9$ photons/s/cm²/steradian. Myogenin was negative for this tumor.

Supplementary FIG. S1. (A) Pharmacokinetics study for 1 in Hairless$^{SKH1/SKH1}$ mice. Mice were injected with 100 μl of 1 intravenously through the tail vein. The first image was captured prior to injection of 1; time thereafter in reference to 1 injection. The images are displayed on a minimum-maximum scale of $1\times10^9$ to $6\times10^9$ photons/s/cm²/steradian. (B) Serial imaging was performed on all 3 mice for 10 days. Clearance Half-life of 1 was approximately 144 hours. Error bars, s.d.

DETAILED DESCRIPTION OF THE INVENTION

Introduction

The present invention provides a fluorescent macromolecular optical contrast agent, pharmaceutical formulations incorporating this agent and methods of optical imaging utilizing this agent. Another object of the present invention is the use of cyanine dyes of the invention for in-vivo diagnosis using near IR (NIR) radiation. Yet another object of the present invention is providing diagnostic reagents that contain compounds of the invention.

Definitions

The following definitions are broadly applicable to each of the embodiments of the present invention set forth hereinbelow. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. The nomenclature used herein and the laboratory procedures in analytical chemistry, and organic synthetic described below are those well known and commonly employed in the art. Standard techniques, or modifications thereof, are used for chemical syntheses and chemical analyses.

The term "alkyl," by itself or as part of another substituent, means, unless otherwise stated, a straight- or branched-chain, or cyclic hydrocarbon radical, or combination thereof, which may be fully saturated, mono- or polyunsaturated and can include mono-, di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, also preferably include those derivatives of alkyl defined in more detail below, such as "heteroalkyl." Alkyl groups that are limited to hydrocarbon groups are termed "homoalkyl". The term "alkyl", as used herein refers to alkyl, alkenyl and alkynyl moieties, each of which can be mono-, di- or polyvalent species. Alkyl groups are preferably substituted, e.g., with one or more groups referred to hereinbelow as an "alkyl group substituent."

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight- or branched-chain, or cyclic alkyl radical consisting of the stated number of carbon atoms and at least one heteroatom selected from the group consisting of B, O, N, Si and S, wherein the heteroatom may optionally be oxidized and the nitrogen atom may optionally be quaternized. The heteroatom(s) may be placed at any internal position of the heteroalkyl group or at a terminus of the chain, e.g., the position through which the alkyl group is attached to the remainder of the molecule. Examples of "heteroalkyl" groups include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Two or more heteroatoms may be consecutive, such as, for example, —CH$_2$—NH—OCH$_3$ and —CH$_2$—O—Si (CH$_3$)$_3$. Similarly, the term "heteroalkylene" by itself or as part of another substituent refers to a substituted or unsubstituted divalent heteroalkyl radical, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linker groups, no orientation of the linker group is implied by the direction in which the formula of the linker group is written. For example, the formula —C(O)$_2$R'— represents —C(O)$_2$R'— and, preferably, —R' C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is meant to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings, one or more of which is optionally a cycloalkyl or heterocycloalkyl), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of "aryl group substituents" described below.

For brevity, the term "aryl" when used in combination with other terms (e.g., aryloxy, arylthioxy, arylalkyl) optionally includes both homoaryl and heteroaryl rings as defined above. Thus, the term "arylalkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" includes groups with carbon atoms bound to groups other than hydrogen, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Exemplary alkyl group substituents include those groups referred to herein as "reactive functional groups" and "linkage fragments."

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_n$—X—$(CR''R''')_d$—, where s and d are independently integers of from 0 to 3, and X is —O—, —NR'—, —S—, —S(O)—, —S(O)$_2$—, or —S(O)$_2$NR'—. The substituents R, R', R'' and R''' are preferably independently selected from hydrogen or substituted or unsubstituted ($C_1$-$C_{16}$)alkyl. Exemplary aryl group substituents include those groups referred to herein as "reactive functional groups" and "linkage fragments."

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The term "salt(s)" includes salts of the compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate, and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts. Hydrates of the salts are also included.

The term "linker" or "L", as used herein, refers to a single covalent bond or a series of stable covalent bonds incorporating 1-30, 2-15, or 5-12 nonhydrogen atoms selected from the group consisting of C, N, O, S and P that covalently link together the components of the solid supports and those of the oligomers of the invention, attaching one component to another. Exemplary linkers include a linkage fragment. Moreover, a linker is of use to attach a carrier molecule and a fluorophore in the contrast agent of the invention. The contrast agents of the invention optionally include a cleavable linker between two components of the contrast agent (e.g., between the carrier molecule and the fluorophore).

A "cleavable linker" is a linker that has one or more cleavable groups that may be broken by the result of a reaction or condition. An exemplary cleavable linker is located within $L^1$, serving to allow for the expedient separation of a carrier molecule and fluorophore. The term "cleavable group" refers to the component of a cleavable linker that is cleaved. Exemplary cleavage mechanisms are enzymatically or otherwise chemically mediated.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, ortho-hydroxcinnamate esters, benzoin esters), and heat. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover a broad range of cleavable, bifunctional (both homo- and hetero-bifunctional) spacer arms are commercially available.

An exemplary cleavable group is cleavable by a reagent, e.g. sodium hydroxide, or ammonia or other amine. In various embodiments the cleavable linker is readily cleaved at room temperature or under microwave conditions.

A "linkage fragment," is a moiety that binds the carrier molecule or the fluorophore to the linker and generally refers to a covalent bond that is formed by reaction of reaction partners, each of which has a reactive functional group of reactivity complementary to the reactivity of its partner. Linkage fragments joining the carrier molecule and the fluorophore to the linker are independently selected. Exemplary linkage fragments include, but are not limited to S, SC(O)NH, HNC(O)S, SC(O)O, O, NH, NHC(O), (O)CNH and NHC(O)O, and OC(O)NH, $CH_2S$, $CH_2O$, $CH_2CH_2O$, $CH_2CH_2S$, $(CH_2)oO$, $(CH_2)oS$ or $(CH_2)oY^x$-PEG wherein, $Y^x$ is S, NH, NHC(O), C(O)NH, NHC(O)O, OC(O)NH, or O and o is an integer from 1 to 50.

The term "fluorophore" as used herein refers to a composition that is inherently fluorescent or demonstrates a change in fluorescence upon binding to a biological compound or metal ion, or metabolism by an enzyme, i.e., fluorogenic. Fluorophores may be substituted to alter the solubility, spectral properties or physical properties of the fluorophore. Numerous fluorophores are known to those skilled in the art and include, but are not limited to coumarin, acridine, furan, dansyl, cyanine, pyrene, naphthalene, benzofurans, quinolines, quinazolinones, indoles, benzazoles, borapolyazaindacenes, oxazine and xanthenes, with the latter including fluoresceins, rhodamines, rosamine and rhodols as well as other fluorophores described in Haugland, MOLECULAR PROBES HANDBOOK OF FLUORESCENT PROBES AND RESEARCH CHEMICALS. Further useful fluorophores are described in commonly owned U.S. Patent Application Publication No. 2005/0214833 and 2005/0170363 and herein below.

The fluorophore may include substituents enhancing a desirable property, e.g., solubility in water, cell permeability and spectral absorption and emission, relative to the "parent" compound in the absence of such substituent. As such the compositions of the invention include substituents that enhance a desirable property relative to an identical parent compound in the absence of the improving substituent.

5-[2-[(1,2-dicarboxyethyl)amino]-2-oxoethyl]-2-[7-[5-[2-[(1,2-dicarboxyet-hyl)amino]-2-oxoethyl]-1,3-dihydro-3,3-dimethyl-1-(4-sulfobutyl)-2H-indol-2-yliden]-1,3,5-heptatrienyl]-3,3-dimethyl-1-(4-sulfobutyl)-3H-indolium, inner salt, potassium hydrogen salt; 2-[7-[5-[2-[(11-carboxy-2-oxo-1,4,7,10-tetraaza-4,7,10-tri(carboxymethyl)-1-undecyl)amino]-2-oxoethyl]-1,3-dihydro-3,3-dimethyl-1-ethyl-2H-indol-2-yliden]-1,3,5-heptatrienyl]-3,3-dimethyl-1-(4- sulfobutyl)-3H-indolium, inner salt; 2-[7-[1,3-dihydro-3,3-dimethyl-S-[2-[(methoxypolyoxyethylene)-amino]-2-oxoethyl]-1-(4-sulfobutyl)-2H-indol-2-yliden]-1,3,5-heptatrienyl]-3,3-dimeth-yl-5-[2-[(methoxypolyoxyethylene)amino]-2-oxoethyl]-1-(4-sulfobutyl)-3H-in-dolium, sodium salt; 2-[7-[1,3-dihydro-3,3-dimethyl-1-(4-sulfobutyl)-2H-indol-2-yliden]-1,3,5-heptatrienyl]-3,3-dimethyl-5-(methoxypolyoxyethylene)aminocarbonyl-1-(4-su-lfobutyl)-3H-indolium, sodium salt; 3-(3-carboxypropyl)-2-[7-[3-(3-carboxypropyl)-1,3-dihydro-3-methyl-1-(4-sulfobutyl)-2H-indol-2-yliden]-1,3,5-heptatrienyl]-3-methyl-1-(4-sulfobutyl-)-3H-indolium, sodium salt; 2-[[3-[[3-(3-carboxypropyl)-1,3-dihydro-3-methyl-1-(4-sulfobutyl)2H-indol-2-yliden]methyl]-2-hydroxy-4-oxo-2-cyclobuten-1-yliden]methyl]-1,1-dimeth-yl-3-ethyl-1H-benz(e)indolium, inner salt; 2-[7-[1,3-dihydro-5-[2-[(2,3-dihydroxypropyl)amino]-2-oxoethyl]-3,3-dimethyl-1-(4-sulfobutyl)-2H-indol-2-yliden]-1,3,5-heptatrienyl]-S-[2-[(2,3-dih-ydroxypropyl)amino]-2-oxoethyl]-3,3-dimethyl-1-(4-sulfobutyl)-3H-indolium, sodium salt.

Cyanine dyes can be synthesized that have a great extinction coefficient when absorbing light at wavelengths from 650 to 120 nm, and that fluoresce with great efficiency. Cyanine dyes of the invention and cyanine dyes used according to the invention are mainly synthesized according to methods known from the literature, for example F. M. Hamer in The Cyanine Dyes and Related Compounds, John Wiley and Sons, New York, 1964; *Cytometry* 10 (1989) 3-10; 11 (1990) 418-430; 12 (1990) 723-730; *Bioconjugate Chem.* 4 (1993) 105-11, *Anal. Biochem.* 217 (1994) 197-204; *Tetrahedron* 45 (1989) 4845-66, European Patent No. EP 0 591 820 A1.

The term "detectable response" as used herein refers to a change in or an occurrence of, a signal that is directly or indirectly detectable either by observation or by instrumentation and the presence or magnitude of which is a function of the presence of a target binding partner for a probe in the test sample. Typically, the detectable response is an optical response resulting in a change in the wavelength distribution patterns or intensity of absorbance or fluorescence or a change in light scatter, fluorescence quantum yield, fluorescence lifetime, fluorescence polarization, a shift in excitation or emission wavelength or a combination of the above parameters. The detectable change in a given spectral property is generally an increase or a decrease. However, spectral changes that result in an enhancement of fluorescence intensity and/or a shift in the wavelength of fluorescence emission or excitation are also useful. The change in fluorescence on ion binding is usually due to conformational or electronic changes in the indicator that may occur in either the excited or ground state of the fluorophore, due to changes in electron density at the ion binding site, due to quenching of fluorescence by the bound target metal ion, or due to any combination of these or other effects. Alternatively, the detectable response is an occurrence of a signal wherein the fluorophore is inherently fluorescent and does not produce a change in signal upon binding to a metal ion or biological compound. The present invention provides probes providing a detectable response and solid supports of use to synthesize such probes.

THE EMBODIMENTS

In various embodiments, the present invention provides macromolecular optical imaging agents. In a representative embodiment, the invention provides a compound having a structure according to Formula I:

$$X-L^1-F \qquad (I)$$

wherein X is a carrier molecule. The symbol $L^1$ represents a linker selected from a bond ("zero-order"), substituted or unsubstituted alkyl, substituted or unsubstituted heteroalkyl, substituted or unsubstituted aryl and substituted or unsubstituted heteroaryl. F is a fluorophore.

The carrier molecule X is selected from a wide range of macromolecular and other species, including without limitation, an amino acid, a peptide, a CDR (complementarity determining regions), an antigen, a hapten, an enzyme substrate, an enzyme cofactor, biotin, a carbotinoid, a hormone, neurohormone, neurotransmitter, a growth factor, a lymphokin, a lectin, a toxin, a carbohydrate, an oligosaccharide, a polysaccharide, a dextran, a cyclodextran, an oligonucleotide made resistant to nucleases or a receptor-bonding pharmaceutical.

Compounds from the above-mentioned groups include, for example, oxytocins, vasopressins, angiotensins, melanocyte-stimulating hormones, somatostatins, tyrotropin-releasing hormones, gonadotropin-releasing hormones, testosterones, estradiols, progesterones, cortisols, aldosterones, vitamin D, gastrins, secretins, somatropins, insulins, glucagons, calcitonin, STH-releasing hormones, prolactins, encephalins, dopamines, noradrenalines, serotonins, epinephrines, interleukines, angiogenins, thymopoietins, erythropoietins, fibrinogens, angiotensinogens, mecamylamines, ranitidine, cimetidine, lovastatines, isoproterenol derivatives or transferrin.

These substances facilitate accumulation in specific parts of the body by targeting the biological detecting unit through certain mechanisms. These mechanisms include bonding to extracellular structures, accumulation through various biological transport systems, recognition of cell surfaces or recognition of intracellular components.

Other compounds can be used according to the invention in which the carrier molecule is a non-selectively bonding macromolecule, such as polylysine, polyethylene glycol, methoxypolyethylene glycol, polyvinyl alcohol, dextran, carboxydextran or a cascade polymer-like structure that is covalently bonded to $L^1$-F.

In various embodiments, the carrier molecule is selected such that the compound of the invention is a blood pool imaging agent. Exemplary agents include thost for which at least 60%, at least 70%, at least 80% or at least 90% of the agent is retained in the blood pool for a time equal to a time course for an NIR imaging experiment. Exemplary time courses include, without limitation, 1 minute, 5 minutes, 10 minutes, 20 minutes, 30 minutes and 60 minutes.

As will be appreciated by those of skill in the art, the contrast agent of the invention can be administered significantly before the imaging experiment is initiated, e.g., 5 h, 8 h, 12 h, 16 h, 20 h, 24 h, 36 h before or more. Exemplary agents of the invention distribute after administration and remain in the blood pool. In various embodiments, the relevant concentration and time course is measured from the initiation of the imaging experiment, rather than from the administration of the agent. Thus, initiation of imaging serves as t=0 for determination of the time course and concentration set forth above.

In an exemplary embodiment, X is a polysaccharide, e.g., cyclodextrin, $L^1$ is a substituted or unsubstituted alkyl linker or substituted or unsubstituted heteroalkyl linker and F is a cyanine, e.g., indocyanine, e.g., indocyanine green. In an exemplary embodiment, the linkage fragment joining the cyclodextrin to the linker includes an amine moiety, e.g., the linker is an alkyl amine. In various embodiments, the linkage fragment joining the linker to the fluorophore is a sulfonamide. In various embodiments, the fluorophore has a maximum absorbance in the range of about 650 nm to about 1200 nm, for example, from about 700 nm to about 900 nm.

One of the advantages of the compounds of the invention is that a wide range of fluorophores can be used in conjunction with the quencher-functionalized solid supports and oligomers. A vast array of fluorophores is known to those of skill in the art. See, for example, Cardullo et al., *Proc. Natl. Acad. Sci.*

USA 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); Wang et al., *Anal. Chem.* 67: 1197-1203 (1995).

A non-limiting list of exemplary fluorophores that can be used in the compounds of the invention is provided in Table 1.

TABLE 1

Suitable moieties for fluorophores in the compounds of the invention 4-acetamido-4'-isothiocyanatostilbene-2,2'disulfonic acid
acridine and derivatives:
    acridine
    acridine isothiocyanate
5-(2''-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
coumarin
    7-amino-4-methylcoumarin (AMC, Coumarin 120)
    7-amino-4-trifluoromethylcouluarin (Coumaran 151)
cyanine dyes
cyanosine
4',6-diaminidino-2-phenylindole (DAPI)
5',5'''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
    fluorescein isothiocyanate
    QFITC (XRITC)
fluorescamine
Indocyanine Green
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:
    pyrene
    pyrene butyrate
    succinimidyl 1-pyrene butyrate
quantum dots
Reactive Red 4 (Cibacron ™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
rhodamine X isothiocyanate
    sulforhodamine B
    sulforhodamine 101

TABLE 1-continued

Suitable moieties for fluorophores in the compounds of the invention sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
lanthanide chelate derivatives There is a great deal of practical guidance available in the literature for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive groups that can be added to a nucleic acid, as exemplified by the following references: Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a nucleic acid, peptide or other polymer.

Means of detecting fluorescent labels are well known to those of skill in the art. Thus, for example, fluorescent labels can be detected by exciting the fluorophore with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product.

In exemplary embodiments, the fluorophore has an absorbance maximum of from about 650 to about 1200 nm, for example, from about Reactive Functional Groups The components of the contrast agents of the invention (e.g., linkers, fluorophore, carrier molecule) are linked through linkage fragments formed by reaction of a first and a second reactive functional group. The reactive functional groups are of complementary reactivity, and they react to form a covalent link between two components of the oligomers referred to herein as a linkage fragment. With reference to the contrast agents of Formula I, the reactive functional group is found on precursors of $L^1$, as well as on precursors of X and F. In various examples, X and $L^1$ are covalently joined through a linkage fragment; $L^1$ and F are joined by a linkage fragment, each linkage fragment formed by reaction of reactive functional groups on the prescursors of the named components of the contrast agents of the invention.

With respect to the precursors of the components of contrast agents of the invention, reactive functional groups, can be located at any position on an aryl or heteroaryl nucleus or a substituent on an aryl or heteroaryl nucleus. Similarly, a reactive functional group is located at any position of an alkyl or heteroalkyl chain. In various embodiments, when the reactive group is attached to an alkyl (or heteroalkyl), or substituted alkyl (or heteroalkyl) chain, the reactive group is preferably located at a terminal position of the chain.

Reactive groups and classes of reactions useful in practicing the present invention are generally those that are well known in the art of bioconjugate chemistry. Currently favored classes of reactions available with reactive precursors of the oligomers of the invention are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

By way of example, reactive functional groups of use in the present invention include, but are not limited to olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

Useful reactive functional group conversions include, for example:

(a) carboxyl groups which are readily converted to various derivatives including, but not limited to, active esters (e.g., N-hydroxysuccinimide esters, N-hydroxybenztriazole esters, thioesters, p-nitrophenyl esters), acid halides, acyl imidazoles, alkyl, alkenyl, alkynyl and aromatic esters;

(b) hydroxyl groups, which can be converted to esters, ethers, halides, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble the oligomer of the invention. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In an exemplary embodiment, the invention provides a compound comprising a cyanine dye of the formula:

in which A and B are independently selected from substituted or unsubstituted aryl and substituted or unsubstituted heteroaryl such that the compound is a fluorescent dye. Q is a substituted or unsubstituted methine moiety (e.g., —(CH=C(R))$_f$—CH=), in which f is an integer selected from 1, 2, 3, 4, or 5 and R is an "alkyl group substituent" as defined herein). Each $R^w$, $R^x$, $R^y$ and $R^z$ is independently selected from those substituents set forth in the Definitions section herein as "alkyl group substituents" and "aryl group substituents." The indices w and z are independently selected from the integers from 0, 1, 2, 3, 4, 5, 6 or greater. In an exemplary embodiment, at least one of $R^w$, $R^x$, $R^y$ and $R^z$ is a linker moiety that includes a first linkage fragment joining the fluorophore to the linker and a second linkage fragment joining the linker to the carrier molecule.

In an exemplary embodiment, the invention provides a compound having the formula:

in which X is a member selected from $CH_3$, OH, COOH and $SO_3H$; a, b, c and d independently represent an integer from 0 to 10, i.e., 0, 1, 2, 3, 4, 5, 6, 7, 8, 9, or 10; and CD is cyclodextrin.

Synthesis

Exemplary compounds of the invention can be prepared by synthetic routes using art-recognized procedures. Exemplary routes are shown in Scheme 1 and Scheme 2:

Scheme 1

Scheme 2

2A

2

The materials and methods of the present invention are further illustrated by the examples which follow. These examples are offered to illustrate, but not to limit the claimed invention.

EXAMPLES

Materials and Methods

Contrast Agent

Compound 1 ($C_{93}H_{132}N_4O_{38}S$) is composed of a β-cyclodextrin ring conjugated to Indocyanine Green (ICG) via a short linker $(CH_2)_6$. 1 has a molecular weight of 1946.11 atomic mass unit (amu). The powdered 1 was freshly constituted with phosphate buffer saline (PBS) to a final concentration of 0.2 mM.

Live Animal Imaging

Optical imaging for all experiments was performed using Xenogen IVIS® Spectrum system (Caliper-Xenogen, Alameda, Calif., USA). All animal procedures were conducted in accordance with the Guidelines for the Care and Use of Laboratory Animals and were approved by the Institutional Animal Care and Use Committee (IACUC) at University of Texas Health Science Center at San Antonio. All images were acquired using epiillumination at excitation wavelength of 745 nm and emission wavelength of 820 nm unless otherwise stated. The camera settings were kept constant at 1 sec exposure time, 4×4 binning, 12.6 cm or 6.5 cm field of view, and f/stop of ½. The data was acquired and analyzed using the manufacturer's Living Image 3.2© software. All animals were imaged using the same anesthesia protocol, 2% isoflurane in 100% oxygen at 2.5 liters per minute. Body temperature was maintained at 37° C. by a heated stage.

Determination of Excitation and Emission Spectra

To determine the excitation and emission spectra for 1, the solution was loaded into a clean cuvette and imaged after 15 minutes using a Xenogen IVIS® Spectrum system. Images were captured using a combined set of excitations ranging from 435 nm to 745 nm (windows of 35 nm) and emission filters ranging from 500 nm to 840 nm (windows of 20 nm).

In Vivo Pharmacokinetics of 1

Hairless$^{SKH1/SKH1}$ mice were obtained from Charles River Laboratories (Wilmington, Mass.). To determine the pharmacokinetics of 1, a group of Hairless$^{SKH1/SKH1}$ mice (n=3) was injected with 100$\mu$4 of 1 in PBS by intravenous tail vein injection and serially imaged for 15 days using the same parameters.

Muscle Injury Model Using Cardiotoxin (CTX)

For myoinjury experiments, twelve-week-old male Hairless$^{SKH1/SKH1}$ mice were intraperitoneally injected with 1 as described above. 60 minutes later, each mouse received intramuscular injections to the anterior compartment muscles below the knee of the right hind limb with 100 µl Cardiotoxin (CTX) (2.5 µM, Calbiochem, San Diego, Calif.), while the left hind limbs in these animals served as non-injected controls. Imaging was performed at intervals 1-240 hours after 1 injection.

In Vivo Tumor Imaging

Mice carrying conditional, the Pax3:Fkhr oncogene and the Patched1 tumor suppressor gene have been previously described (3,4). In this study, three transgenic mice with spontaneous tumors were evaluated. These animals were a Myf6$^{ICNm/WT}$ Pax3$^{P3Fm/P3Fm}$ Trp53$^{F2-10/F2-10}$ Rb1$^{Flox/Flox}$ mouse bearing a neck tumor, a Pax7$^{CreER/WT}$ Pax3$^{P3Fm/P3Fm}$ Trp53$^{F2-10/F2-10}$ mouse bearing a back tumor and a Pax7$^{CreER/WT}$ Trp53$^{F2-10/F2-10}$ PTC1$^{F1-2m/WT}$ mouse with a face tumor. All animals were injected with 100 µl 1 intravenously and imaged 24 hours after injection. The animals were then euthanized and tumor tissue was collected for pathology studies.

Results and Discussion

Figure 1:
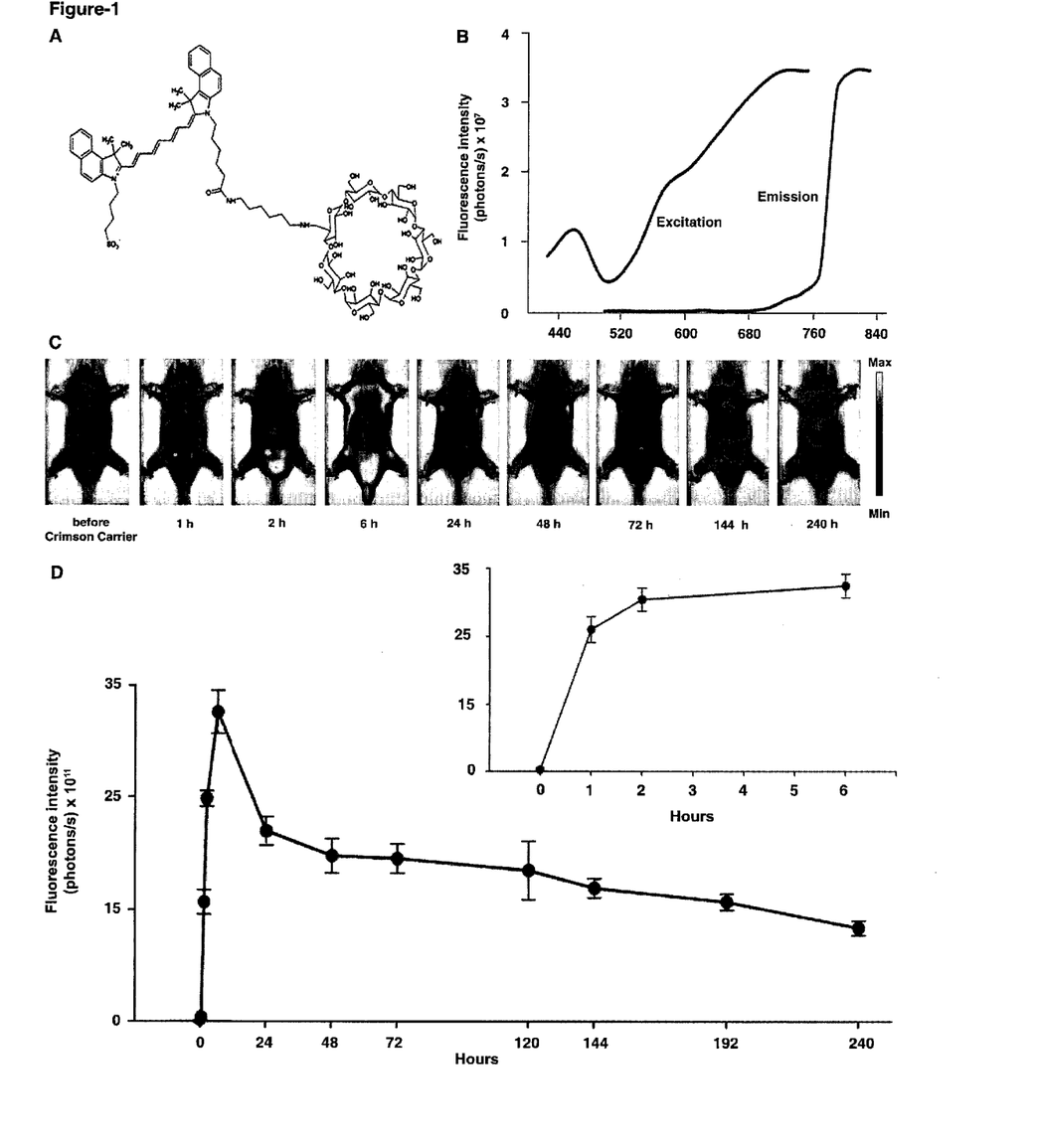
FIG. 1 (A) Chemical structure of Compound B. (B) Spectra for free 1 reveal excitation and emission maxima at 745 nm and 820 nm respectively. (C) Pharmacokinetics study for 1 in Hairless$^{SKH1/SKH1}$ mice. Mice were injected with 100 µL of 1 intraperitoneally. The first image was captured prior to injection of 1; time thereafter in reference to Compound 1 injection. The images are displayed on a minimum-maximum scale of $3\times10^9$ to $1\times10^{10}$ photons/s/cm²/steradian. (D) Serial imaging was performed on all 3 mice for 10 days. Clearance Half-life of 1 was approximately 144 hours. Error bars, s.d.
Figure 1:
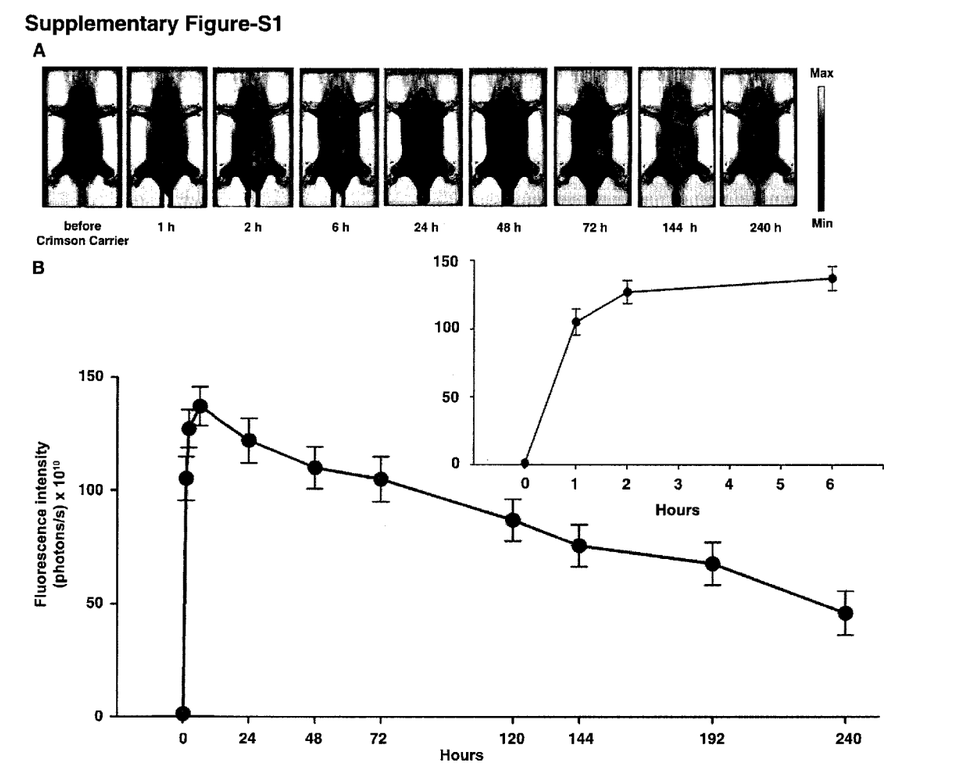

Compound 1 (FIG. 1A) is a chimerical molecule consisting of a β-cyclodextrin ring to a near infrared moiety modified for improved urinary excretion. The peaks for excitation and emission wavelengths for 1 were measured to be 745 nm and 820 nm, respectively (FIG. 1B). Pharmacokinetics experiments were performed to determine distribution and clearance under non-injury conditions. Following intraperitoneal injection, the fluorescence signal intensity of 1 steadily increased and peaked 6 hours after administration (FIG. 1C). The pharmacokinetics studies show the clearance half-life of this agent to be 144 hours with intraperitoneal administration (FIG. 1D). Clearance was primarily urinary (data not shown). No overt toxicity was observed in 1-injected animals monitored as long as 10 weeks.

Figure 2:
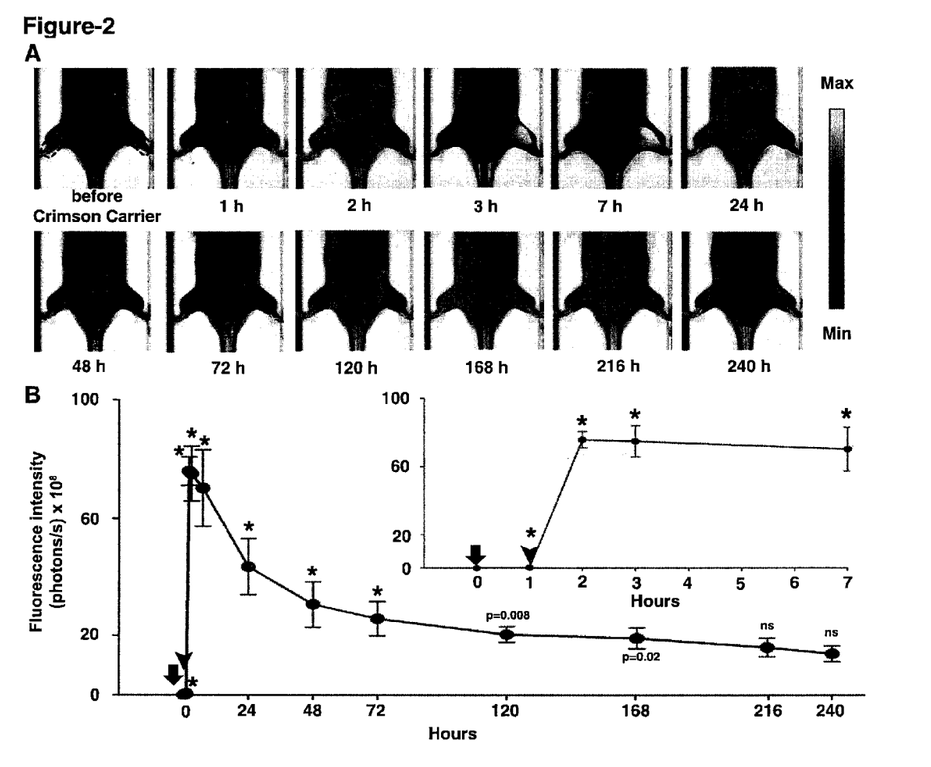

A well-established cardiotoxin (CTX) mouse injury model (5) was used to determine the efficacy of 1 in monitoring capillary leak. CTX contains lytic factors whose primary mechanism of action is forming pores that depolarize and degrade the muscle plasma membrane (6). CTX was injected intramuscularly into the anterior compartment of the right hind limb muscles of Hairless$^{SKH1/SKH1}$ mice while the left non-injected hind limb was considered as the control. To determine the extent of injury-induced 1 leak into the extravascular space, the signal intensity of the right and left hind limb regions were measured and the paired difference of the injected (right) hind limb signal intensity to the non-injected (left) hind limb signal intensity was calculated (FIG. 2B). With CTX injection, an immediate 1500 fold increase in the paired difference occurred at the 2-hour time point suggesting an increased extravascular 1 signal in the injected hind limb, which far exceeded the intravascular 1 signal of the contralateral, non-injected hind limb. The paired difference in the CTX group was significantly elevated compared to baseline from the 2 to 72-hour time points. These data suggest that capillary leak begins within 1 hour after injury and that ongoing leak and/or decreased clearance continues for as long as 72 hours. This time course is consistent with the inflammatory and regenerative response previously reported for the CTX injury model (5,7).

Figure 3:
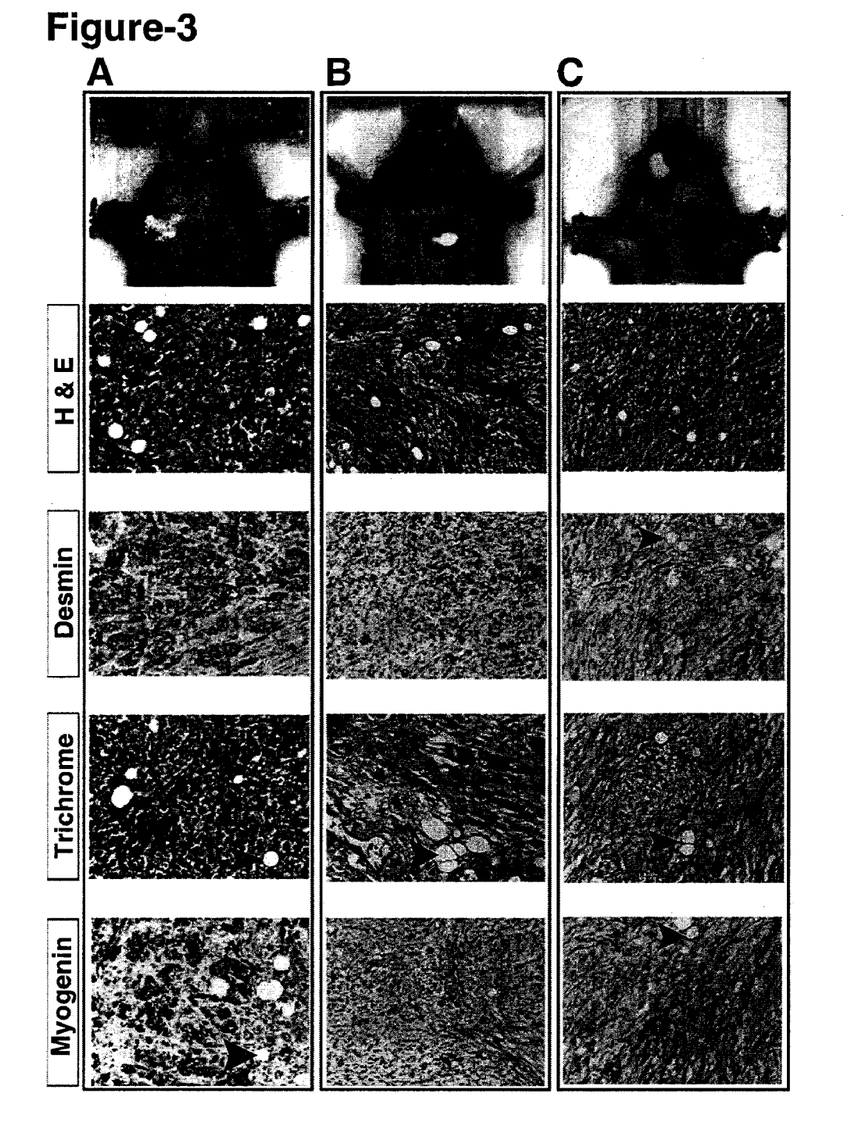

To detect capillary leak often associated with cancers, three transgenic mice with solid tumors (rhabdomyosarcoma) were injected intravenously with 100 µL of 0.2 mM 1 and imaged 24 hours later. Results in FIG. 3A-C show the rate of clearance of 1 in case of altered vascular conditions. The bright fluorescence from tumor image confirmed that the presence of 1 occurs from the actual tumor and not on the skin surface overlying the tumor (data not shown). Histology and immunohistochemistry not only confirm the diagnoses of these solid tumors as rhabdomyosarcoma but also highlight the number of capillaries and small vessels seen in these tumors. Thus, 1 has utility not only for determining the time course of capillary leak with muscle injury, but also for detection of altered tumor vascular beds.

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

REFERENCES

1. Grimm, J., D. G. Kirsch, S. D. Windsor, C. F. Kim, P. M. Santiago, V. Ntziachristos, T. Jacks, and R. Weissleder. 2005. Use of gene expression profiling to direct in vivo molecular imaging of lung cancer. *Proc. Natl. Acad. Sci. USA* 102:14404-14409.
2. Luker, G. D. and K. E. Luker. 2008. Optical imaging: current applications and future directions. *J. Nucl. Med.* 49:1-4.
3. Taniguchi, E., M. J. Cho, B. R. Arenkiel, M. S. Hansen, O. J. Rivera, A. T. McCleish, S. J. Qualman, D. C. Guttridge, et al. 2009. Bortezomib reverses a post-translational mechanism of tumorigenesis for patched1 haploinsufficiency in medulloblastoma. *Pediatr. Blood Cancer.*
4. Nishijo, K., T. Hosoyama, C. R. Bjornson, B. S. Schaffer, S. I. Prajapati, A. N. Bahadur, M. S. Hansen, M. C. Blandford, et al. 2009. Biomarker system for studying muscle, stem cells, and cancer in vivo. *FASEB J.*
5. Ochoa, O., D. Sun, S. M. Reyes-Reyna, L. L. Waite, J. E. Michalek, L. M. McManus, and P. K. Shireman. 2007. Delayed angiogenesis and VEGF production in CCR2−/− mice during impaired skeletal muscle regeneration. *Am. J. Physiol. Regul. Integr. Comp. Physiol.* 293:R651-661.
6. Harris, J. B. 2003. Myotoxic phospholipases A2 and the regeneration of skeletal muscles. *Toxicon* 42:933-945.
7. Prajapati, S. I., C. O. Martinez, A. N. Bahadur, I. Q. Wu, W. Zheng, J. D. Lechleiter, L. M. McManus, G. B. Chisholm, et al. 2009. Near-infrared Imaging of Injured Tissue in Living Subjects Using IR-820. *Mol. Imaging.* 8:45-54.

What is claimed is:

1. A compound having the formula:

in which
X is a member selected from —$CH_3$, —COOH, and —$SO_3H$
a, b, c, and d are independently selected integers from 1 to 10; and
CD is cyclodextrin.

2. A pharmaceutical formulation comprising the compound according to claim 1 and a pharmaceutically acceptable carrier.

* * * * *